US011918776B1

(12) United States Patent
Haigh et al.

(10) Patent No.: US 11,918,776 B1
(45) Date of Patent: Mar. 5, 2024

(54) MULTI-POSITIONAL HANDLE FOR INTRAVENOUS BAG STAND

(71) Applicant: CENTICARE Corporation, Minnetonka, MN (US)

(72) Inventors: James H. Haigh, Eden Prairie, MN (US); Preston Haigh, Minnetonka, MN (US)

(73) Assignee: CENTICARE Corporation, Minnetonka, MN (US)

( * ) Notice: Subject to any disclaimer, the term of this patent is extended or adjusted under 35 U.S.C. 154(b) by 0 days.

(21) Appl. No.: 17/858,034

(22) Filed: Jul. 5, 2022

Related U.S. Application Data

(60) Provisional application No. 63/217,858, filed on Jul. 2, 2021.

(51) Int. Cl.
*A61M 5/14* (2006.01)
*F16M 11/42* (2006.01)

(52) U.S. Cl.
CPC .......... *A61M 5/1415* (2013.01); *F16M 11/42* (2013.01); *F16M 2200/06* (2013.01)

(58) Field of Classification Search
CPC ......... A61M 5/1415; A61J 1/16; F16M 11/42; F16M 2200/06
See application file for complete search history.

(56) References Cited

U.S. PATENT DOCUMENTS

| | | | |
|---|---|---|---|
| 4,225,104 A | 9/1980 | Larson | |
| 4,832,294 A | 5/1989 | Eidem | |
| 5,236,213 A * | 8/1993 | Trickett | F16M 11/42 403/97 |
| 5,479,953 A | 1/1996 | Pasulka | |
| 5,915,712 A | 6/1999 | Stephenson et al. | |
| 6,101,678 A * | 8/2000 | Malloy | B62B 5/06 403/DIG. 4 |
| 6,390,311 B1 | 5/2002 | Belokin | |
| 6,581,246 B1 * | 6/2003 | Polette | A01D 34/90 16/444 |
| 6,969,031 B2 * | 11/2005 | Ugent | A61M 5/1415 248/129 |
| 7,497,407 B2 | 3/2009 | Blakenship et al. | |
| 7,500,689 B2 | 3/2009 | Pasternak et al. | |

(Continued)

FOREIGN PATENT DOCUMENTS

CA 2549229 6/2005

*Primary Examiner* — Anita M King
(74) *Attorney, Agent, or Firm* — DuFault Law Firm, P.C.; Dustin R. DuFault

(57) ABSTRACT

A two-position handle device for use with a wheeled intravenous bag holder having a vertical pole includes a collar slidably positionable upon the vertical pole. A first member extends from the collar, the first member having a tenon extending therefrom, while a second member connects to the first member, the second member having a tenon extending therefrom. A handle extends from the second member, wherein the handle is positionable between a first downwardly extending position and a second horizontally extending position. To lock the handle in the second position, a cylindrical sleeve slidably disposes over both the tenon of the second member and the tenon of the first member, thereby preventing pivotal movement of the second member relative to the first member, and locking the handle in the second horizontally extending position.

7 Claims, 6 Drawing Sheets

(56) References Cited

U.S. PATENT DOCUMENTS

| | | | |
|---|---|---|---|
| 7,637,464 B2 | 12/2009 | Heimbrock et al. | |
| 7,641,158 B2 | 1/2010 | Ferguson | |
| 7,694,606 B1 | 4/2010 | Williams | |
| 7,823,256 B2 * | 11/2010 | Engelfried | B25F 5/026 |
| | | | 16/426 |
| 7,935,030 B1 | 5/2011 | Nesbitt | |
| 8,641,078 B2 | 2/2014 | Yang | |
| 9,144,708 B2 * | 9/2015 | Selek | A63B 23/03541 |
| 9,669,155 B2 | 6/2017 | Chepurny | |
| 9,834,118 B2 * | 12/2017 | Kunkel | B62B 7/02 |
| 10,426,887 B2 | 10/2019 | Koehler et al. | |
| 10,752,277 B2 | 8/2020 | Haigh | |
| 11,617,913 B2 * | 4/2023 | Anderson | A63B 21/4035 |
| | | | 482/139 |
| 2003/0132614 A1 * | 7/2003 | Kreamer | A63B 23/16 |
| | | | 280/647 |
| 2013/0228997 A1 | 9/2013 | Fukuhara et al. | |

* cited by examiner

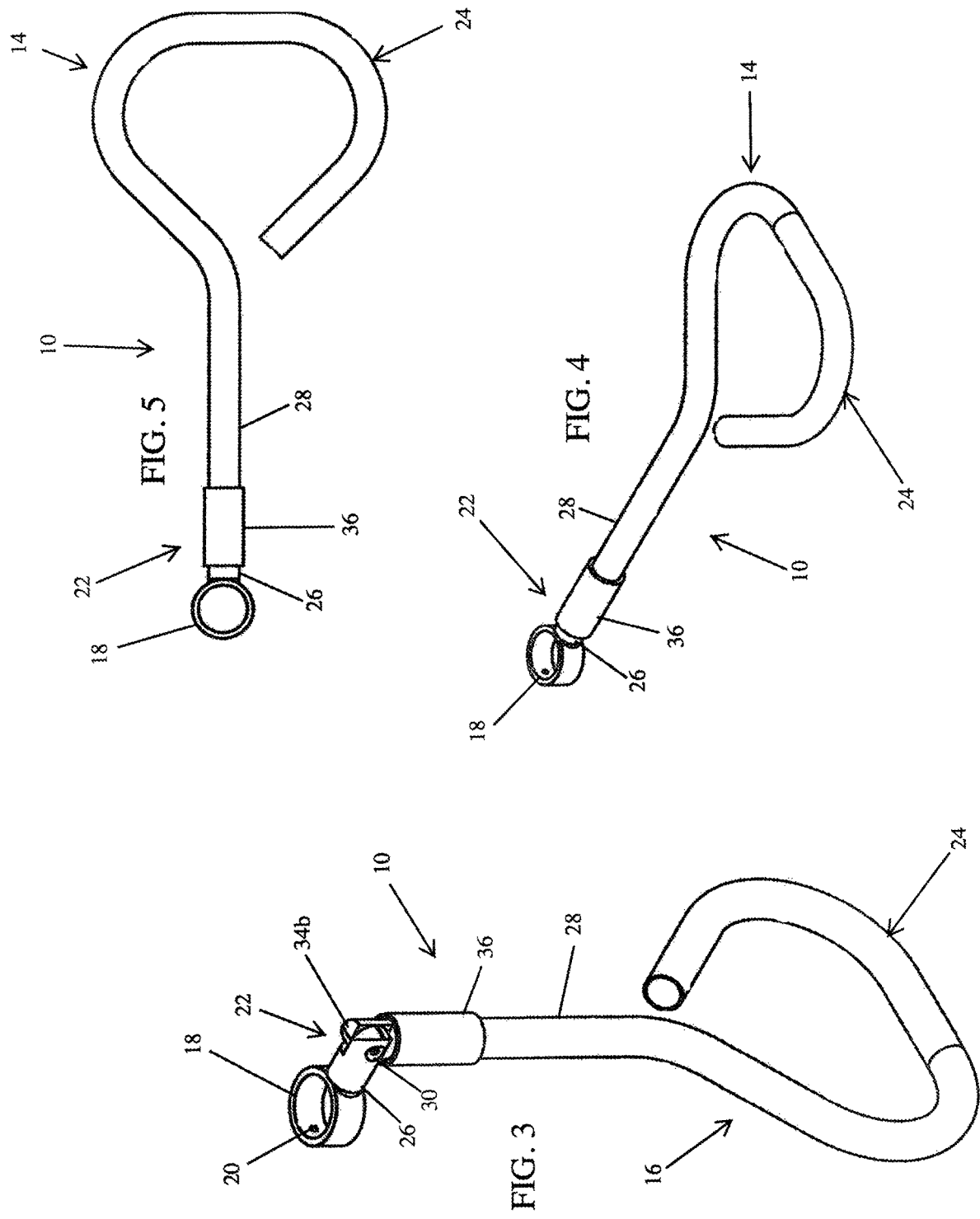

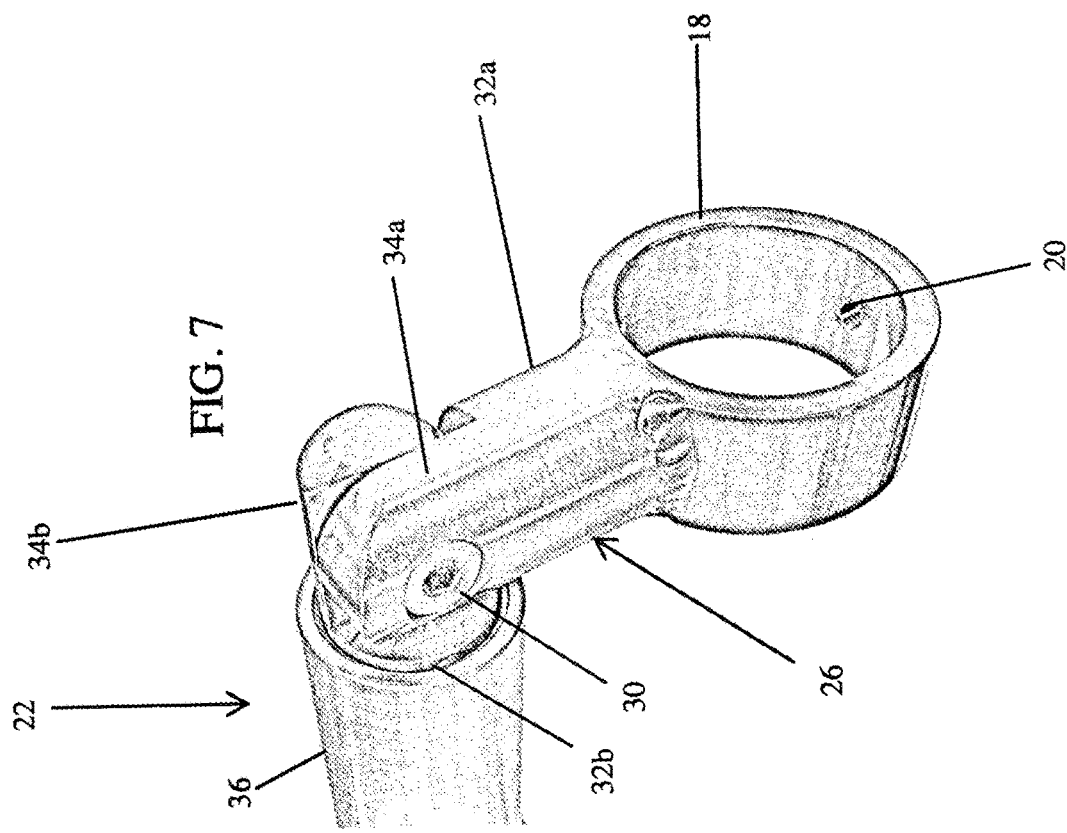
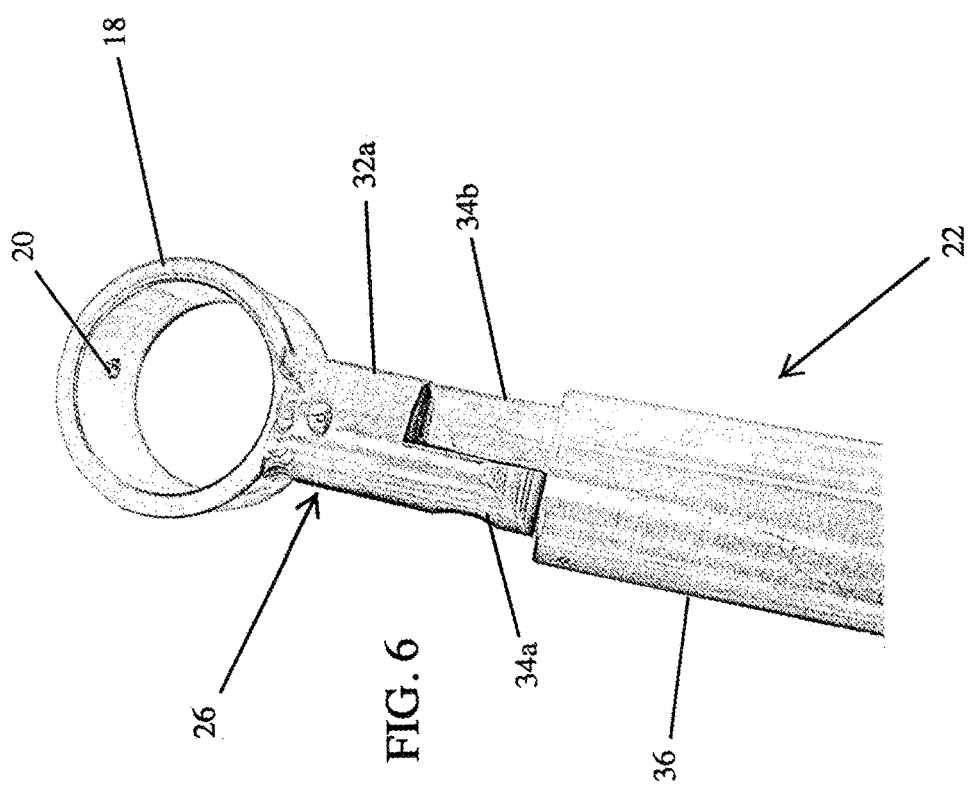

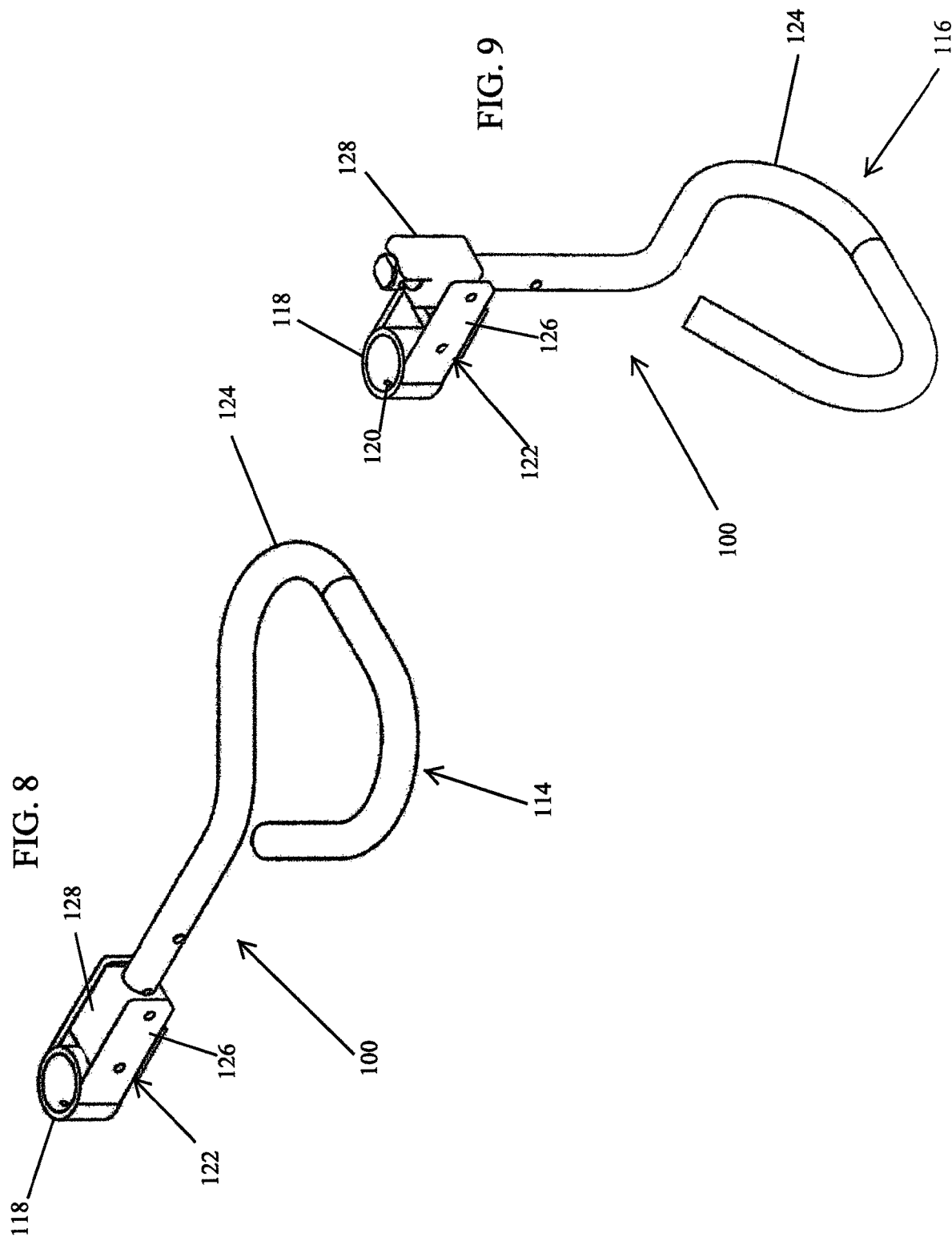

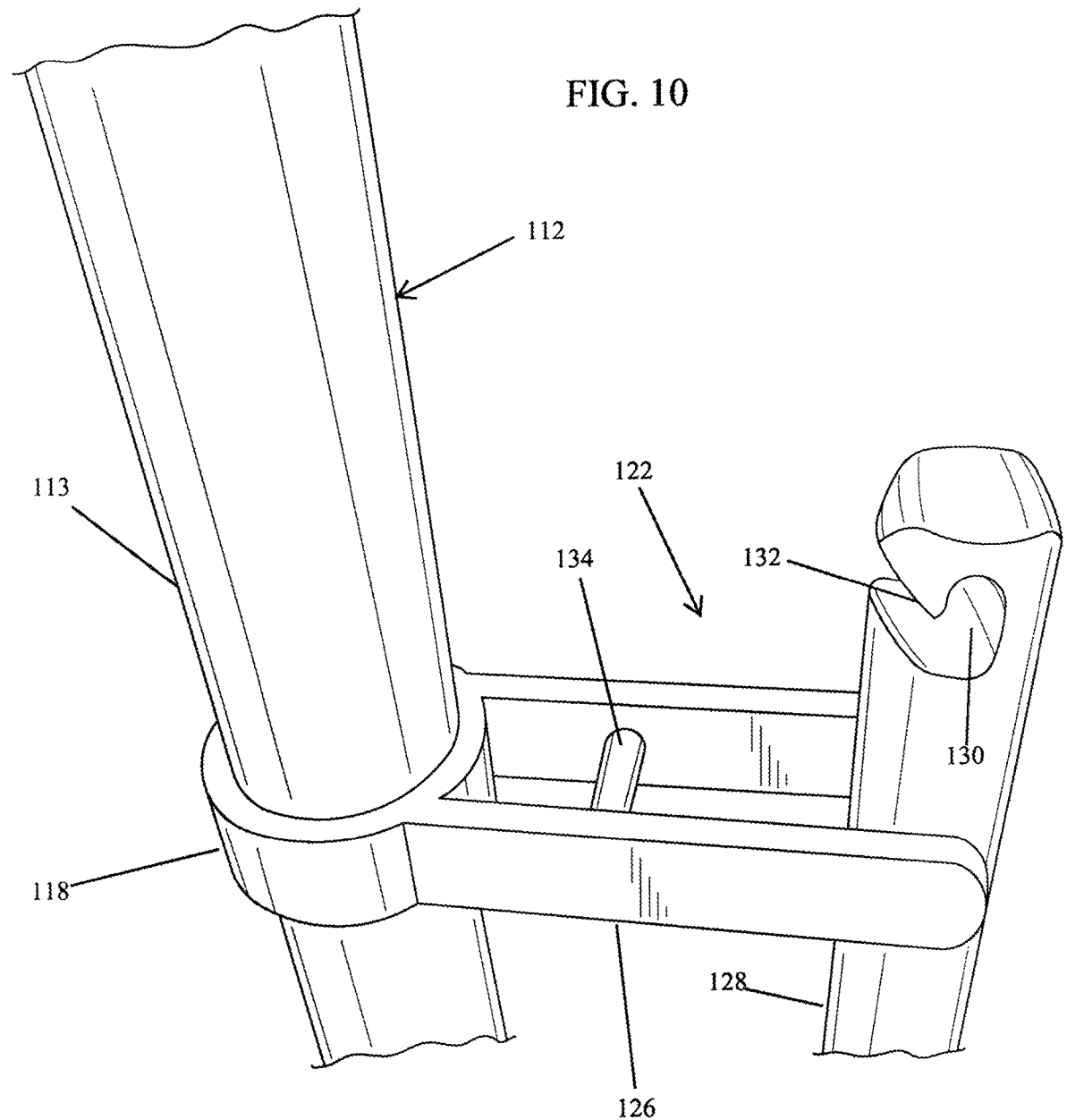

MULTI-POSITIONAL HANDLE FOR INTRAVENOUS BAG STAND

CROSS-REFERENCE TO RELATED APPLICATION

The present application claims a benefit of similarly entitled U.S. Provisional Application No. 63/217,858 filed Jul. 2, 2021, the contents of which are incorporated herein by reference.

BACKGROUND OF THE INVENTION

The present invention is generally directed at intravenous bag stands. More particularly, the present invention includes a repositionable handle attachable to an intravenous bag stand wherein the handle is positionable between a first generally downward non-working position for storage, and a second generally horizontal working position for use in moving the intravenous bag stand.

In the medical industry, an intravenous bag is oftentimes supported by a stand on caster wheels so that the patient can be moved or walk about while connected to the intravenous bag. If the patient desires to move or walk about while connected to the intravenous bag, it has been the practice that the patient simply grab the upright pole of the stand to move or position the stand. However, oftentimes, this leads to the patient being in close proximity to the base of the stand, including the legs holding the caster wheels. In certain circumstances, this has lead to the patient coming into contact with the base, sometimes leading to the patient tripping or falling, causing further injury. Moreover, if a handle extends a distance greater than the wheelbase of the stand, this creates issues when storing the stands when not in use as the protruding handles do not lead to conducive and efficient storage of the stands.

There therefore exists a need in the art to provide a handle attachable to an intravenous bag stand which is not bulky, is not burdensome to use, and can be easily manipulated from a working to non-working position such that the patient can use the stand without coming into accidental contact with the base of the stand.

BRIEF SUMMARY OF INVENTION

The present invention includes a two-position handle device for use with an intravenous bag stand of the prior art. The device is positionable between a first generally downward non-working position for storage, and a second generally horizontal working position for use in moving the intravenous bag stand. The device generally comprises a first collar member attachable to a vertical pole of the intravenous bag stand, a second handle member pivotally connected to the first collar member, and a locking mechanism to lock the second member in the second horizontal working position. The locking mechanism comprises a cylindrical sleeve slidable over a tenon of the first collar member and a tenon of the second handle member. The tenons have similar dimensions, with each configured to have semi-circular portions and a flat sidewall or face. The tenons pivotally connect to one another by means of an internal fastener, such as a bolt and threaded nut.

The locking sleeve is positionable between a first unlocked position and a second locked position. In the first unlocked position, neither tenon fully disposes within the sleeve, which engages only a portion of the second handle member, thereby permitting the tenons to freely pivot relative to one another. In the second locked position, the sleeve disposes over both tenons after positioning the handle member horizontally, thereby locking the tenons in place.

BRIEF DESCRIPTION OF THE DRAWINGS

The following figures are used herein in conjunction with the specification to assist in understanding the invention. The Figures are as follows:

FIG. 3 is a perspective view of the multi-positional handle in a non-working position in accordance with the first embodiment of the present invention.

FIG. 4 a perspective view of the multi-positional handle in a working position in accordance with the first embodiment of the present invention.

FIG. 5 a top view of the multi-positional handle in a working position in accordance with the first embodiment of the present invention.

FIG. 6 is a partial perspective view of a pivoting assembly of the multi-positional handle in accordance with the first embodiment of the present invention.

FIG. 7 is a partial perspective view of the multi-positional handle in accordance with the first embodiment of the present invention.

FIG. 8 is a perspective view of a multi-positional handle in a working position in accordance with a second embodiment of the present invention.

FIG. 9 is a perspective view of the multi-positional handle in a non-working position in accordance with a second embodiment of the present invention.

FIG. 10 is a partial perspective view of the multi-positional handle in a non-working position in accordance with a second embodiment of the present invention.

DESCRIPTION OF THE INVENTION

Figure 1:
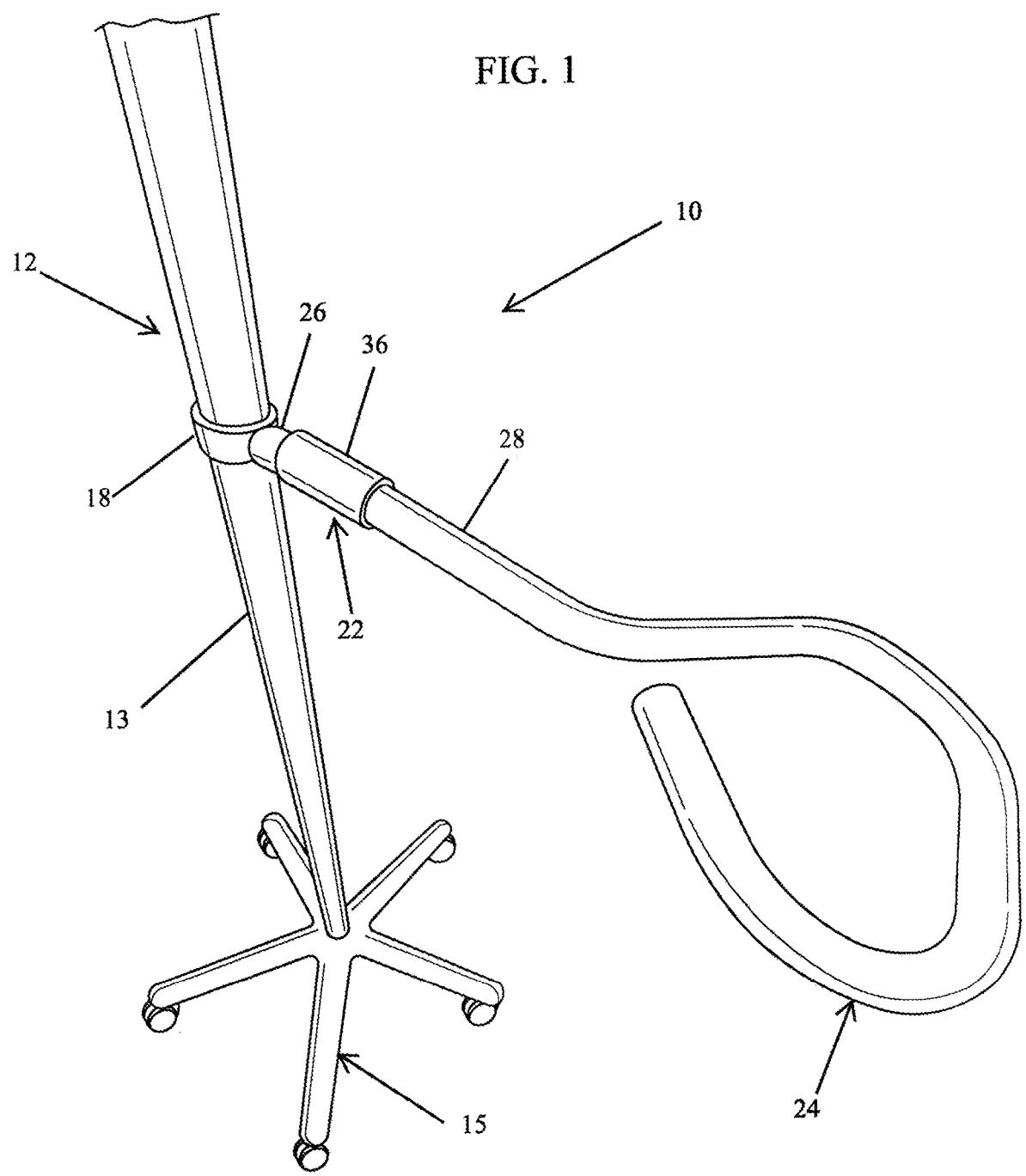
FIG. 1 is a front perspective view a multi-positional handle attached to an intravenous bag stand while in a working position in accordance with a first embodiment of the present invention.
Figure 2:
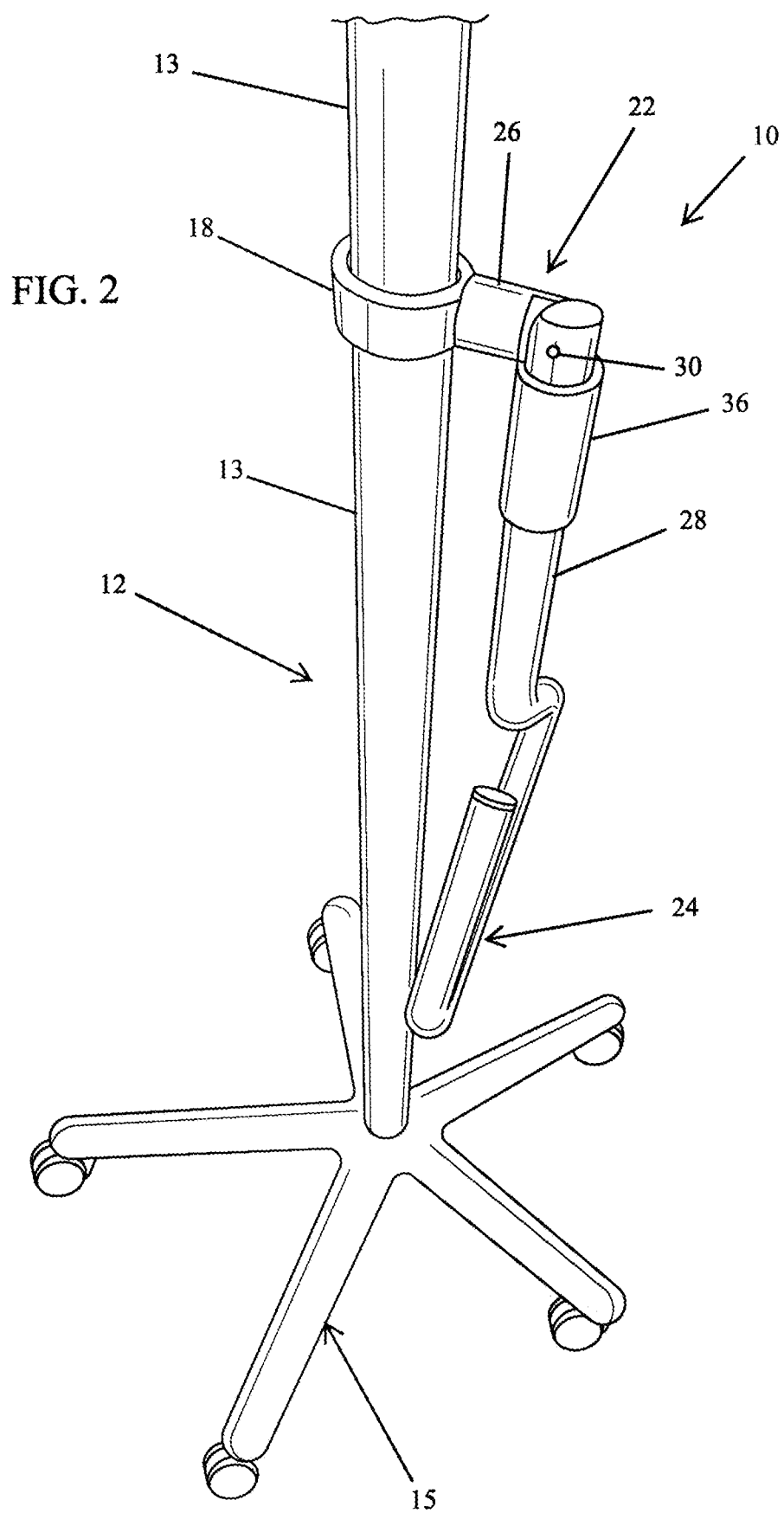
FIG. 2 is a perspective view of the multi-positional handle attached to an intravenous bag stand while in a non-working position in accordance with the first embodiment of the present invention.

Referring to FIGS. 1 and 2, a multi-positional handle in accordance with a first embodiment of the present invention is generally indicated at 10. The multi-positional handle 10 is preferably used in conjunction with an intravenous bag stand, as is known to those skilled in the art, as generally indicated at 12. For purpose of this description, the intravenous bag stand 12 generally has a vertical pole 13 supported by a wheeled base 15. The multi-positional handle 10 connects to the pole 15 and is positionable between a generally horizontally extended working position 14, as illustrated in FIGS. 1, 4 and 5, and a generally downwardly extending non-working, or storage, position 16, as illustrated in FIGS. 2 and 3.

The multi-positional handle 10 includes a collar 18 attachable to the pole 13 of the intravenous bag stand 12. The collar 18 preferably contains a fastening device 20 which allows the collar 18 to be slidably positioned vertically along the pole 13 to a selected or desired height, whereupon the fastening device 20 can be manipulated to frictionally engage the collar 18, and thus handle 10, at that selected or desired height. This is advantageous when the same stand 12 is used among different patients of differing height, wherein the preferably height of the handle is at or slightly above the waist of the patient. Attached to and extending from the collar 18 is a proximal end of a locking mechanism 22. A handle 24 extends from a distal end of the locking mechanism 22.

The locking mechanism 22 includes a first segment 26 attached to the collar 18, and a second segment 28 attached to the handle 24. The first segment 26 and the second segment 28 pivotally mate with one another, each being connected via a connecting fastener or screw 30. As illustrated in FIGS. 6 and 7, the first segment 26 and the second segment 28 are configured to have a first main body portion 32a and 32b, respectively, from which extends an attaching ear or tenon 34a and 34b, respectively. Both the first segment 26 and the second segment 28 are of similar outer dimensions. Each mating face of the tenons 34a, 34b is preferably flat such that the first segment 26 pivotally mates with the second segment 28 by engaging a face of each attaching ear 34a, 34b together, wherein the fastener or screw 30 disposes within an aperture contained therein.

Returning to FIGS. 3 through 5, the locking mechanism 22 further includes a sliding cylindrical sleeve 36 which is positionable between a locking position, as illustrated in FIGS. 4 and 5, and a non-locking position, as illustrated in FIG. 3. The cylindrical sleeve 36 has an internal diameter only slightly larger than that of either the first or second segments 26, 28, such that the first and second segments 26, 28 may slidably dispose therein. The sleeve 36 further includes an internal divot (not shown) that prevents the sleeve 36 from fully sliding down the handle 24 while in the non-locking position 16, as well as maintaining the sleeve 36 while in the locked position.

In operation, to position the handle 24 from the non-working, or storage, position 16, into the locked working position 14, a user manipulates the handle 24 to pivot from the generally downward vertically oriented position to the generally horizontal position. With the handle 24 positioned generally horizontally, the user then manipulates the sliding sleeve 36 over the first segment 26 and the second segment 28 of the locking mechanism 22. Upon positioning the sliding collar 28 in this manner, the second segment 28 is not permitted to move relative to the first segment 26, and the handle 24 is locked generally horizontally into place. While locked into the working position, a user can grasp the handle 24 and maneuver the intravenous bag stand 12.

When maneuvering the intravenous bag stand 12 is no longer needed, and it is either desirable to be stored, or reposition the handle so as not to be obstrusive or in the way, the handle 24 can be unlocked and positioned to the non-working, or storage, position 16 by manipulating the sliding sleeve 36 of the locking mechanism 22 from the first segment 26 and second segment 28 and onto the shaft 25 of the handle 24 such that the sliding collar 36 no longer covers the first and second segment 26, 28 of the locking mechanism 22, whereby the second segment 28 is permitted pivotal movement relative to the first segment 26, and the handle 24 can be lowered from the generally horizontal position 14 to the generally downward, non-working position 16. The intravenous bag stand 12, or the like, can then be stored or set aside until needed again.

Referring now to FIGS. 8 through 10, a multi-positional handle in accordance with a second embodiment of the present invention is generally indicated at 100. The multi-positional handle 100 is also preferably used in conjunction with intravenous bag stands 112, as was the first embodiment 10. The multi-positional handle 100 is positionable between a generally horizontally extended working position 114, as illustrated in FIG. 8, and a generally vertically downwardly extended non-working, or storage, position 116, as illustrated in FIG. 10.

The multi-positional handle 100 includes a collar 118 attachable to a vertical pole 113 of the intravenous bag stand 112 in the same manner as the preferred embodiment 10. The collar 118 preferably contains a fastening device 120 which allows the collar 118 to be positioned vertically along the pole of the intravenous bag stand 112 at a selected or desired position. Attached to and extending from the collar 118 is a proximal end of a locking mechanism 122. A handle 124 extends from a distal end of the locking mechanism 122.

The locking mechanism 122 includes a first segment 126 attached to the collar 118, and a second segment 128 attached to the handle 124. The first segment 126 and the second segment 126 are pivotally connected to one another, with the second segment 128 permitted longitudinal travel relative to the first segment 126. The second segment 128 includes a cavity portion 130 having a tooth 132 extending inwardly into the cavity 130. The first segment 126 of the locking mechanism 122 includes a round cross bar 134 extending from one side to the other. The second segment 128 mates with the first segment 126 by pivoting the handle 124 to position the tooth 132 of the second segment 128 to engage and lock to the round cross bar 134 of the first segment 126.

In operation, to position the handle 124 from the non-working, or storage, position, into the locked working position, a user manipulates the handle 124 to pivot from the generally vertical position to the generally horizontal position. With the handle 124 positioned generally horizontally, the user then urges the tooth 132 of the second segment 128 past the cross bar 134 of the first segment 126, such that the cross bar 134 nests within the cavity 130 of the second segment 128. Upon positioning the tooth 132 in this manner, the user pulls back on the handle 124, thereby engaging the tooth 132 with the cross bar 134, which prevents any further pivotal movement of the handle 124 and locks the handle 124 in place. While locked into the working position, a user can grasp the handle and maneuver the intravenous bag stand 112.

When maneuvering the intravenous bag stand 112 is no longer needed, such as when the intravenous bag stand is put way to be stored, the handle 124 can be unlocked and positioned to the non-working, or storage, position 114, by pushing the handle 124 inward to disengage the tooth 132 from the cross bar 134, thereby permitting the second segment 128 pivotal movement relative to the first segment 126, and the handle 124 can be lowered to the generally downward, non-working position 114.

It is recognized there are multiple variations beyond what are outlined in the detailed description to accomplish the objectives set forth by the current invention. Further alternative embodiments provide additional utility of the device for the convenience of the user. As such, although the present invention has been described with reference to preferred and alternative embodiments, workers skilled in the art will recognize that changes may be made in form and detail without departing from the spirit and scope of the invention.

The invention claimed is:

1. A two-position handle device for use with a wheeled intravenous bag holder having a vertical pole, the device comprising:

a collar slidably positionable on the vertical pole of the intravenous bag holder;

a first member extending from the collar;

a second member pivotally connected to the first member;

a handle connected to the second member; and a locking mechanism to lock the first member and the second member together while the handle is positioned extending generally horizontal to the ground, the locking mechanism including:

a first tenon extending from the first member;

a second tenon extending from the second member, the first tenon and the second tenon each having similar dimensions and pivotally connected to one another; and a cylindrical sleeve, whereupon aligning the second tenon in the same plane as the first tenon, the cylindrical sleeve is slidably disposable over the first tenon and the second tenon to prevent any further pivotal movement of the second tenon relative to the first tenon.

2. The handle device of claim 1 wherein the first tenon and the second tenon are each configured to have a flat sidewall, wherein the sidewall of the first tenon engages the sidewall of the second tenon.

3. A two-position handle device for use with a wheeled intravenous bag holder having a vertical pole, the device comprising:

a collar slidably positionable on the vertical pole of the intravenous bag holder;

a first member extending from the collar;

a second member pivotally connected to the first member;

a handle extending from the second member; and a locking mechanism to lock the handle in a horizontally extending position, the locking mechanism including a cylindrical member disposed upon the second member, whereupon positioning the handle in the horizontally extending position, the cylindrical member is permitted to be slidably disposed upon both the second member and first member, thereby preventing pivotal movement of the second member relative to the first member.

4. The handle device of claim 3 wherein the locking mechanism further comprises:

a first tenon extending from the first member;

a second tenon extending from the second member, the first tenon and the second tenon each having similar dimensions and pivotally connected to one another; and wherein the cylindrical member is slidably disposable over the first tenon and the second tenon to prevent pivotal movement of the second tenon relative to the first tenon.

5. The handle device of claim 4 wherein the first tenon and the second tenon are each configured to have a flat sidewall, wherein the sidewall of the first tenon engages the sidewall of the second tenon.

6. A two-position handle device for use with a wheeled intravenous bag holder having a vertical pole, the device comprising:

a collar slidably positionable on the vertical pole of the intravenous bag holder;

a first member extending from the collar, the first member having a tenon extending therefrom;

a second member connected to the first member, the second member having a tenon extending therefrom;

a handle extending from the second member, the handle positionable between a first downwardly extending position and a second horizontally extending position; and a cylindrical member disposed upon the second member, wherein the tenon the second member pivotally attaches to the tenon of the fir member, whereupon positioning the handle to the horizontally extending position, the cylindrical member is permitted to be slidably disposed upon both the tenon of the second member and the tenon of the first member, thereby preventing pivotal movement of the second member relative to the first member, locking the handle in the second horizontally extending position.

7. The handle device of claim 6 wherein the tenon of the first member and the tenon of the second member are each configured to have a flat sidewall, wherein the sidewall of the tenon of the first member engages the sidewall of the tenon of the second member.

* * * * *